United States Patent [19]

Harada et al.

[11] Patent Number: 4,667,027

[45] Date of Patent: May 19, 1987

[54] CEPHEM COMPOUNDS AND THEIR PRODUCTION

[75] Inventors: Setsuo Harada, Kawanishi; Yukimasa Nozaki, Ikeda; Hideo Ono, Kobe, all of Japan

[73] Assignee: Takeda Chemical Industries, Ltd., Osaka, Japan

[21] Appl. No.: 681,783

[22] Filed: Dec. 14, 1984

[30] Foreign Application Priority Data

May 7, 1984 [JP] Japan .................................. 59-91314
Aug. 10, 1984 [JP] Japan .................................. 59-168691

[51] Int. Cl.[4] .................. A61K 31/545; C07D 501/40
[52] U.S. Cl. .................................... 549/221; 540/230; 514/201; 514/209; 530/331
[58] Field of Search ........................ 544/21, 30; 260/112.5 R; 514/201, 209

[56] References Cited

FOREIGN PATENT DOCUMENTS 114752 8/1984 European Pat. Off. .
114750 8/1984 European Pat. Off. .
2107307 4/1983 United Kingdom .

OTHER PUBLICATIONS

Hamilton—Miller, et al., "Products of Aninolysis . . . of Cephalosporins", *Biochem. J.* (1970), 116, 371-381.
*The Journal of Antibiotics*, vol. 37, No. 7, pp. 773-780, (1984).
Program and Abstracts of the Twenty—Fourth Interscience Conference on Antimicrobial Agents and Chemotherapy, p. 292, (1984), No. 1139.

*Primary Examiner*—Glenna M. Hendricks
*Attorney, Agent, or Firm*—Wenderoth, Lind & Ponack

[57] ABSTRACT

A compound of the formula:

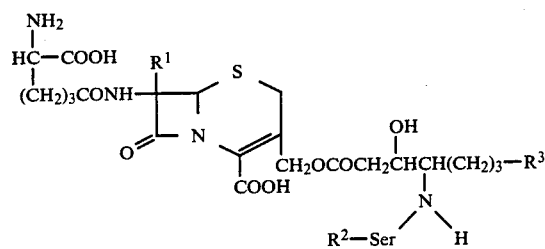

wherein $R^1$ stands for hydrogen or formylamino, $R^2$ is a residue of amino acid selected from the group consisting of serine and alanine, or a peptide of at least one of these amino acids, or hydrogen, $R^3$ stands for —NH—C(=NH)—NH$_2$ or —CH$_2$NH$_2$, or its salt, which can be produced by cultivating a microorganism belonging to the genus Xanthomonas, is useful as a therapeutic agent against infectious disease caused by bacteria.

14 Claims, 9 Drawing Figures

CEPHEM COMPOUNDS AND THEIR PRODUCTION

The present invention relates to novel cephem compounds which are useful as therapeutic agents against infectious disease caused by bacteria, and to their production.

The compounds most widely used as a starting material for cephem antibiotics are penicillin G and cephalosporin C, and both of these are the products of fermentation by fungi. The fermentation by fungi generally requires a prolonged period of time of fermentation, and this is responsible for increased costs and lessened energy-saving and presents a problem of vital importance from the standpoint of fermentation production.

In recent years, abuse of cephem antibiotics has resulted in an increasing number of organisms resistant to such antibiotics, which has become a problem from the viewpoint of clinical medicine. Cephem antibiotics are the most valuable antibiotic in terms of selective toxicity, and consequently, a cephem antibiotic which is stable or resistant to cephalosporinases is regarded as exceptionally important.

The present inventors, with a specific view to the search for novel antibiotics, isolated a large number of microorganisms from soils or plants and performed screenings for identifying the antibiotics which the microorganisms produce. As a result, it was found that a certain microorganism is able to produce a novel antibiotic, that said microorganism belongs to a novel species of the genus Xanthomonas, and that cultivation of said microorganism in a suitable culture medium results in accumulation of the antibiotic which exhibits antimicrobial activity against gram-positive and negative bacteria including resistant bacteria in the medium. The inventors isolated these antibiotics, and ascertained from their physicochemical and biological properties that they are novel cephem antibiotics. The present inventors conducted further research based on these findings, and have completed the present invention.

The present invention is directed to
(1) A compound of the formula:

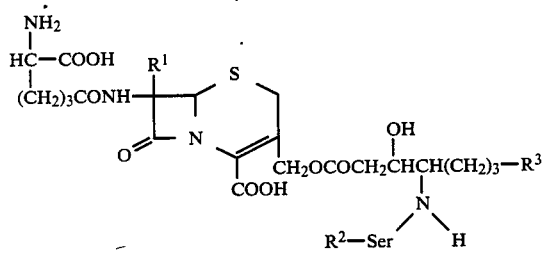

wherein $R^1$ stands for hydrogen or formylamino, $R^2$ is a residue of amino acid selected from the group consisting of serine and alanine, or a peptide of at least one of these amino acids, or hydrogen, $R^3$ stands for $-NH-C(=NH)-NH_2$ or $-CH_2NH_2$, or its salt, and (2) A method for producing the compound (I), which comprises cultivating a microorganism belonging to the genus Xanthomonas and being capable of elaborating the compound (I) in a culture medium to have the compound (I) accumulated in the culture broth and harvesting the compound (I) or its salt.

In the formula, —Ser— represents

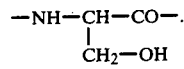

The residue of serine represents

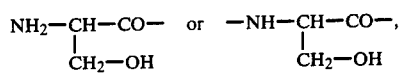

and the residue of alanine represents

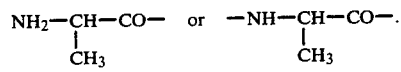

As the residue of amino acid or peptide, the serine residue (i.e.

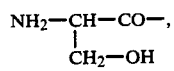

which is sometimes represented as Ser—), or alanine residue-serine residue (i.e.

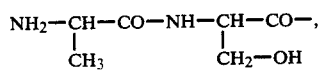

which is sometimes represented as Ala—Ser—) are particularly preferable.

Formylamino represents

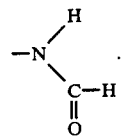

In the present specification, the compounds shown by the formula (I) are named as follows:

| Antibiotic | $-R^1$ | $R^2-$ | $-R^3$ |
|---|---|---|---|
| TAN-592A | —NH—CHO | H— | $-NH-\overset{NH}{\underset{\|}{C}}-NH_2$ |
| TAN-592B | —NH—CHO | Ser— | $-NH-\overset{NH}{\underset{\|}{C}}-NH_2$ |
| TAN-592C | —NH—CHO | Ala—Ser— | $-NH-\overset{NH}{\underset{\|}{C}}-NH_2$ |
| TAN-592D | —H | H— | $-NH-\overset{NH}{\underset{\|}{C}}-NH_2$ |
| TAN-592E | —H | Ser— | $-NH-\overset{NH}{\underset{\|}{C}}-NH_2$ |
| TAN-592F | —H | Ala—Ser— | $-NH-\overset{NH}{\underset{\|}{C}}-NH_2$ |
| TAN-591A | —NH—CHO | H— | $-CH_2-NH_2$ |
| TAN-591B | —NH—CHO | Ser— | $-CH_2-NH_2$ |

-continued

| Antibiotic | —R$^1$ | R$^2$— | —R$^3$ |
|---|---|---|---|
| TAN-591C | —NH—CHO | Ala—Ser— | —CH$_2$—NH$_2$ |

In this specification, the term "Antibiotic TAN-592" or the abridged term "TAN-592" will be sometimes used in order to refer to the individual Antibiotic TAN-592A, B, C, D, E or F, or a mixture containing at least two of them, and the term "Antibiotic TAN-591" or the abridged term "TAN-591" will be sometimes used in order to refer to the individual Antibiotic TAN-591A, B or C, or a mixture containing at least two of them.

As the Antibiotic TAN-592 producing strain which is used in this invention, any and all microorganisms may be employable, only if they belong to the genus Xanthomonas and are capable of producing Antibiotic TAN-592.

Their examples include a new species of microorganism, *Xanthomonas lactamgena*. As specific examples thereof, there may be mentioned *Xanthomonas lactamgena* YK-280 (hereinafter sometimes referred to briefly as "Strain YK-280") which was isolated from a plant sample collected at Ayama District, Mie Prefecture, Japan.

The microbiological characteristics of Strain YK-280 are described in the following.

(a) Morphology

Observation after the cultivation on a nutrient agar slant at 24° C. for 5 days reveals that cells are in the form of rod having a diameter of 0.2 to 0.8 μm and a length of 0.6 to 1.0 μm; and that the microorganism exhibits motility by means of flagellum, has a single polar flagellum, does not form spore and is gram-negative and not acid-fast.

(b) Growth on various culture media

Observation was made during the cultivation at 24° C. over the period of 1 to 14 days.

(1) Nutrient agar plate culture: Translucent, lemon-yellow and circular colonies having a raised or convex surface, with entire edge. No diffusible pigment produced.

(2) Nutrient agar slant culture: Good, glistening and spread-cloth like growth. Opaque and yellow.

(3) Nutrient broth culture: Turbid growth, with faint ringformed. Sediment observed.

(4) Nutrient gelatin stab culture: Good growth mainly on the surface. Stratiform liqufaction, with strong liquefaction activity.

(5) Litmus milk: No ability of reducing litmus observed. Weak peptonization activity noticed, but no coagulation observed.

(c) Physiological characteristics.

(1) Reduction of nitrates: —
(2) Denitrification: —
(3) MR (Methyl red) test: —
(4) VP (Voges-Proskauer) reaction: —
(5) Production of indole: —
(6) Production of hydrogen sulfide (lead acetate paper): +
(7) Hydrolysis of starch: +
(8) Utilization of citric acid (Koser's, Christensen's and Simmons' culture media): +
(9) Utilization of inorganic nitrogen source
(I) Potassium nitrate: —
(II) Ammonium sulfate: +
(10) Production of pigments (King A and B and mannitol-yeast extract agar culture media): Yellow intracellular pigment observed in the King B culture medium, but no diffusible pigment produced.

King A culture medium: 10 g of glycerol, 20 g of 1.4 g of magnesium chloride, 10 g of ammonium sulfate, 15 g of agar, 1000 ml of distilled water, pH 7.2.

King B culture medium: 10 g of glycerol, 20 g of peptone, 1.5 g of potassium monohydrogenphosphate, 1.5 g of magnesium sulfate, 15 g of agar, pH 7.2.

(11) Urease: —
(12) Oxidase: +
(13) Catalase: +
(14) Ranges of growth:
(I) pH: Growth at pH 4.6 to 8.3, with the optimum pH being 6.2 to 7.3.
(II) Temperature: Growth at 11° to 40° C., with the optimum temperature being 16° to 26° C.
(15) Oxygen demand: Aerobic.
(16) O-F(oxidative-fermentative) test (Hugh-Leifson method): Not reactive in the initial stage of cultivation but oxidative in the final stage.
(17) Production of acid and gas from sugars:

|  | Acid Peptone-water | Gas Peptone-water | Utilization (Davis medium) |
|---|---|---|---|
| L-Arabinose | ± | — | + |
| D-Xylose | — | — | + |
| D-Glucose | — | — | + |
| D-Mannose | — | — | + |
| D-Fructose | — | — | + |
| D-Galactose | — | — | + |
| Maltose | — | — | + |
| Sucrose | — | — | + |
| Lactose | — | — | + |
| Trehalose | — | — | + |
| D-Sorbitol | — | — | — |
| D-Mannitol | — | — | — |
| Inositol | — | — | — |
| Glycerol | — | — | + |
| Starch | — | — | + |

+: Positive,
±: false positive,
—: negative

(18) GC (guanine+cytosine) content in DNA: 75.7±1.5%.
(19) NaCl tolerance: 0 to 4%.
(20) The ability to decompose carboxymethylcellulose and coloidal chitin: +
(21) The ability to decompose agar and alginate: —
(22) The ability to decompose Tween 80: + (rapid)

Comparison of Strain YK-280 having the above microbiological characteristics with the species described in Bergey's Manual of Determinative Bacteriology, 8th edition, International Journal of Systematic Bacteriology, 30, 225-420 (1980) and ibid., Validation List demonstrates that Strain YK-280 is a gram-negative rod exhibiting motility by means of monotrichous flagellum and containing a yellow carotenoid pigment, it is aerobic, with a high GC content in DNA and it lacks the ability to reduce nitrates but decomposes rapidly starch and Tween 80. These observations suggest that it is appropriate and reasonable to consider the strain as belonging to the genus Xanthomonas. Therefore, Strain YK-280 was compared with the known species of the genus Xanthomonas as described in the above literature references. As the known species of the genus Xanthomonas, there have been known only five species. Comparison of the characteristics of Strain YK-280 with the descriptions of these five species led us to inability to find any known strain of microorganism which shared all of the below described characteristics with Strain YK-280, namely that (1) the gelatin liquefaction activity is positive, (2) the oxidase activity is positive, (3) neither acid nor gas from glucose and mannose is produced, and (4) the strain can grow in the presence of 4% of sodium chloride.

In view of the above, we identified Strain YK-280 as a strain belonging to a novel species, and named said novel species of microorganism *Xanthomonas lactamgena*.

The above *Xanthomonas lactamgena* YK-280 has been deposited as of Mar. 20, 1984 at the Institute for Fermentation, Osaka (IFO), Japan under the deposit number of IFO 14330. This microorganism has also been deposited as of Apr. 28, 1984 at the Fermentation Research Institute, Agency of Industrial Science and Technology, Ministry of International Trade and Industry (FRI), Japan under the deposit number of FERM P-7602, and the deposit has been converted to a deposit under the Budapest Treaty and has been stored at FRI under the accession number of FERM BP-635.

As the Antibiotic TAN-591 producing strain which is used in this invention, any and all microorganisms may be employable, only if they belong to the genus Xanthomonas and are capable of producing Antibiotic TAN-591. Their examples include a new species of microorganism, *Xanthomonas lactamgena*. As specific examples thereof, there may be mentioned *Xanthomonas lactamgena* YK-278 (hereinafter sometimes referred to briefly as "Strain YK-278") which was isolated from a plant sample collected at Ayama District, Mie Prefecture, Japan.

The microbiological characteristics of Strain YK-278 are described in the following.

(a) Morphology

Observation after the cultivation on a nutrient agar slant at 24° C. for 5 days reveals that cells are in the form of rod having a diameter of 0.2 to 0.8 μm and a length of 0.6 to 1.0 μm; and that the microorganism exhibits motility by means of flagellum, has a single polar flagellum, does not form spore and is gram-negative and not acid-fast.

(b) Growth on various culture media.

Observation was made during the cultivation at 24° C. over the period of 1 to 14 days.

(1) Nutrient agar plate culture: Translucent, lemon-yellow and circular colonies having a raised or convex surface, with entire edge. No diffusible pigment produced.

(2) Nutrient agar slant culture: Good, glistening and spread-cloth like growth. Opaque and yellow.

(3) Nutrient luqid cultue: Turbid growth, with faint ringformed. Sediment observed.

(4) Nutrient gelatin stab culture: Good growth mainly on the surface. Stratiform liquefaction, with strong liquefaction activity.

(5) Litmus milk: No ability of reducing litmus observed. Weak peptonization activity noticed, but no coagulation observed.

(c) Physiological characteristics
 (1) Reduction of nitrates: −
 (2) Denitrification: −
 (3) MR (Methyl red) test: −
 (4) VP (Voges-Proskauer) reaction: −
 (5) Production of indole: −
 (6) Production of hydrogen sulfide (lead acetate paper): ±
 (7) Hydrolysis of starch: +
 (8) Utilization of citric acid (Koser's, Christensen's and Simmons' culture media): +
 (9) Utilization of inorganic nitrogen source
 (I) Potassium nitrate: +
 (II) Ammonium sulfate: ±
 (10) Production of pigments (King A and B and mannitol-yeast extract agar culture media): Yellow, intracellular pigment observed in the three culture media, but no diffusible pigment produced.

King A culture medium: 10 g of glycerol, 20 g of 1.4 g of magnesium chloride, 10 g of ammonium sulfate, 15 g of agar, 1000 ml of distilled water, pH 7.2.

King B culture medium: 10 g of glycerol, 20 g of peptone, 1.5 g of potassium monohydrogenphosphate, 1.5 g of magnesium sulfate, 15 g of agar, pH 7.2.

(11) Urease: −
 (12) Oxidase: +
 (13) Katalase: +
 (14) Ranges of growth:
 (I) pH: Growth at pH 4.6 to 8.3, with the optimum pH being 6.9 to 7.7.
 (II) Temperature Growth at 14° to 38° C., with the optimum temperature being 18° to 25° C.
 (15) Oxygen demand: Aerobic.
 (16) O-F(oxidative-fermentative) test (Hugh-Leifson method): Not reactive in the initial stage of cultivation but oxidative in the final stage.
 (17) Production of acid and gas from sugars:

| | Acid Peptone-water | Gas Peptone-water | Utilization (Davis medium) |
|---|---|---|---|
| Arabinose | − | − | + |
| D-Xylose | − | − | + |
| D-Glucose | − | − | + |
| D-Mannose | − | − | ± |
| D-Fructose | − | − | + |
| D-Galactose | − | − | + |
| Maltose | − | − | + |
| Sucrose | − | − | + |
| Lactose | − | − | + |
| Trehalose | − | − | + |
| D-Sorbitol | − | − | ± |
| D-Mannitol | − | − | − |
| Inositol | − | − | − |
| Glycerol | − | − | + |
| Starch | − | − | + |

+: positive,
±: false positive,
−: negative

(18) GC (guanine+cytosine) constant in DNA: 74.4±1.5%.
(19) NaCl tolerance: 0 to 4%.
(20) The ability to decompose carboxymethylcellulose and alginate: +
(21) The ability to decompose agar and coloidal chitin: −
(22) The ability to decompose Tween 80: + (rapid)

Comparison of Strain YK-278 having the above microbiological characteristics with the species described in Bergey's Manual of Determinative Bacteriology, 8th edition, International Journal of Systematic Bacteriology, 30, 225-420 (1980) and ibid., Validation List demonstrates that Strain YK-278 is a gram-negative bacillus exhibiting motility by means of monotrichous flagellum and containing a yellow carotenoid pigment, it is aerobic, with a high GC content in DNA and it lacks the ability to reduce nitrates but decomposes rapidly starch and Tween 80. These observations suggest that it is appropriate and reasonable to consider the strain as belonging to the genus Xanthomonas. Therefore, Strain YK-278 was compared with the known species of the genus Xanthomonas as described in the above literature references. As the known species of the genus Xanthomonas, there have been known only five species. Comparison of the characteristics of Strain YK-278 with the descriptions of these five species led us to inability to find any known strain of microorganism which shared all of the below described characteristics with Strain YK-278, namely in that (1) the gelatin liquefaction activity is positive, (2) the oxidase activity is positive, (3) neither acid nor gas from glucose and mannose is produced, and (4) the strain can grow in the presence of 4% of sodium chloride.

In view of the above, we identified that Strain YK-278 belongs to said novel species *Xanthomonas lactamgena,* and named said microorganism *Xanthomonas lactamgena* YK-278.

The above *Xanthomonas lactamgena* YK-278 has been deposited as of June 18, 1984 at the Institute for Fermentation, Osaka (IFO), Japan under the deposit number of IFO 14351. This microorganism has also been deposited as of June 25, 1984 at the Fermentation Research Institute, Agency of Industrial Science and Technology, Ministry of International Trade and Industry (FRI), Japan under the deposit number of FERM P-7681, and the deposit has been converted to a deposit under the Budapest Treaty and has been stored at FRI under the accession number of FERM BP-636.

Said strain has an ability to produce TAN-592 A, B, C, D, E and F in addition to TAN-591. The components of TAN-592 were isolated from the filtrate of the cultured broth of the strain, and the components were proved to be identical with TAN-592 standard sample in terms of the physico-chemical properties of thin layer chromatography, high performance liquid chromatography, ultraviolet absorption spectrum, infrared absorption spectrum, circular dichroism spectrum, molecular weight (SIMS method), and so forth.

The microorganism of the genus Xanthomonas which is used in the present invention is generally liable to vary its characteristics, and can be easily caused to undergo mutation by artificial mutation means using for example ultraviolet light, X-rays and chemical agents (e.g., nitrosoguanidine, ethylmethanesulfonic acid, etc.). Any of such mutants can also be used in the present invention insofar as they are capable of producing the compound (I) of the present invention.

In the cultivation of the compound (I) producing strain, as the carbon source, use is suitably made of carbon sources which are assimilable to the strain, such as glucose, maltose, lactose, spent molasses, fats and oils (e.g., soybean oil, olive oil, etc.) and organic acids (e.g., citric acid, succinic acid, gluconic acid, etc.). As the nitrogen source, organic nitrogen compounds and inorganic nitrogen compounds, such as soybean meal, cottonseed meal, corn steep liquor, dried yeast, yeast extract, meat extract, peptone, urea, ammonium sulfate, ammonium nitrate, ammonium chloride and ammonium phosphate, can be utilized. As the inorganic salt, inorganic salts which are normally required for the cultivation of microorganisms, such as sodium chloride, potassium chloride, calcium carbonate, magnesium sulfate, monopotassium phosphate and disodium phosphate, are used solely or in suitable combination. If sulfur compounds which the compound (I) producing strain can assimilate, such as inorganic sulfur compounds exemplified by sulfates (e.g., ammonium sulfate. etc.), thiosulfates (e.g., ammonium thio-sulfate, etc.) and sulfites (e.g., ammonium sulfite, etc.), organic sulfur compounds exemplified by sulfur-containing amino acids (e.g., cystine, cysteine, L-thiazolidine-4-carboxylic acid, etc.), hypotaurine and sulfur-containing peptides (e.g., glutathion, etc.) or mixtures thereof, are added to the culture medium, the production amount of the objective compound may be sometimes increased.

Furthermore, heavy metals such as ferrous sulfate and copper sulfate, vitamins such as vitamin $B_1$ and biotin, and so forth are added, if desired. In addition, antifoams such as silicone oil and polyalkylene glycol ether and surface active agents may be added. Other organic and inorganic materials which can support the growth of the microorganism and promote the production of the compound (I) may be suitably added.

With reference to the cultural method, the cultivation may be conducted in the same manner as the processes for the production of common antibiotics, and may be by means of the solid or liquid cultural method. In the case of liquid culture, any of stationary culture, submerged culture, shake culture, aerated culture, etc. may be conducted, though submerged aerobic culture is particularly preferable. The temperature of incubation is preferably in the range of about 10° C. to 30° C., preferably 17° to 24° C., and the cultivation is carried out over the pH range of about 4 to 8, preferably 6 to 7, for 8 to 168 hours, preferably for 24 to 144 hours.

For recovering the objective compound (I), the conventional isolation means employed in the harvesting of metabolites produced by a microorganism from the microbial culture is suitably utilized. Since the compound (I) is provided with properties of aqueous basic substance (the antibiotic, which contains weakly acid functional groups too, is a basic substance as the whole molecule) and is contained predominantly in the filtrate of the cultured broth, for example, a filter aid is in the first place added to the cultured broth and microbial cells are removed by filtration or centrifugation; the resulting filtrate is contacted with a suitable support to adsorb the active ingredient in the filtrate, and the active ingredient is desorbed with a suitable solvent. Such means of isolation and harvesting is advantageously utilized. As the support or adsorbent for chromatography, advantageous use is made of those utilizing the difference in adsorptive power of compounds such as activated carbon, silica gel, powdery cellulose and adsorptive resins, those taking advantage of the difference in functional group of compounds such as cationic exchange resins, cationic exchange cellulose and cationic exchange Sephadex, and those utilizing the difference in molecular weight of compounds such as Sephadex products. In order to elute the objective compound from these supports, for example, aqueous solutions of water soluble organic solvents such as aqueous acetone and aqueous alcohols, or aqueous solutions containing acid, alkali, buffer or inorganic or organic salts are used in suitable combinations, which vary depending upon the type and nature of supports.

Also, the crude product containing the antibiotic as obtained by these chromatographic procedures is subjected to preparative high-performance liquid chromatography (HPLC) for separation to yield the purified product.

In more particular, when a cationic exchange resin such as Dowex-50W (produced by Dow Chemical Co., U.S.A.), Amberlite IR-120 and 200 (produced by Rohm & Haas Co., U.S.A.) and Diaion SK 116 (produced by Mitsubishi Chemical Industries, Ltd., Japan) is employed as a support, the antimicrobial substance in the filtrate is adsorbed on the support, and then eluted with an aqueous solution containing salts, acids or buffer, etc. Alternatively, the antibiotic can be adsorbed on such a support as cationic exchange, molecular sieve resin, for example CM-Sephadex (Pharmacia Fine Chemicals, Sweden), and eluted with an aqueous solution containing salts or acids or buffer, etc. In order to remove salts, coloring materials, etc. in these eluates, activated carbon for chromatographic use (produced by Takeda Chemical Industries, Ltd., Japan) or adsorptive resins such as Diaion HP-20 (produced by Mitsubishi Chemical Industries, Ltd., Japan) and Amberlite XAD-II (produced by Rohm & Haas Co., U.S.A.) are advantageously employed. The eluates fractionated are powdered by subjecting to steps such as concentration and lyophilization. For the purpose of further purification when the purity of the powder thus obtained is low, preparative HPLC method is advantageously used. As the support which is useful in the method, there may be mentioned, for example, TSK Gel (produced by Toyo Soda Mfg. Co., Japan), YMC Gel (produced by Yamamura Chemical Laboratories, Japan), etc., and as the mobile phase, use is made of mixtures of methanol or acetonitrile, etc. with aqueous solutions containing inorganic salts or buffer, etc. The compound (I) is isolated in the form of a mono-, di- or tri-pharmaceutically acceptable salt with mineral acids such as hydrochloric acid, sulfuric acid and phosphoric acid or organic acids such as formic acid, acetic acid and oxalic acid.

The physico-chemical properties of Antibiotic TAN-592 . hydrochloride obtained in Example 1 which appears hereinafter are shown below.

TAN-592A . dihydrochloride:
(1) Appearance: white powder.
(2) Molecular weight: SIMS metnod, $(M+H)^+$ 704.
(3) Molecular formula: $C_{26}H_{41}N_9O_{12}S.2HCl\ (2H_2O)$.

| (4) Elemental analysis (%): | |
|---|---|
| Found*[1] | Calcd.*[2] |
| C, 38.49 ± 2.0 | C, 38.43 |
| H, 6.03 ± 1.0 | H, 5.83 |
| N, 15.63 ± 1.5 | N, 15.51 |
| | O, 27.56 |
| S, 4.22 ± 1.0 | S, 3.95 |
| Cl, 7.95 ± 1.5 | Cl, 8.73 |

*[1] The sample was dried over diphosphorus pentoxide for 8 hours at 60° C. under reduced pressure.
*[2] The value is calculated as the sample contains 2 moles of water.

(5) Ultraviolet absorption (UV) spectrum: $\lambda_{max}^{H2O}$ 260±2 nm ($E_{1\ cm}^{1\%}$ =124±20).
(6) Circular dichroism (CD) spectrum: $[\theta]_{226\pm2}^{H2O}$ −32,000±5000 and $[\theta]_{258\pm2}^{H2O}$ +28,000±5000.
(7) Infrared absorption (IR) spectrum: Main wave number (cm$^{-1}$) in KBr tablet: FIG. 1 3420, 3080, 2960, 1780, 1730, 1670, 1510, 1400, 1260, 1170, 1060, 980, 860, 510.
(8) Nuclear magnetic resonance ($^{13}$C-NMR) spectrum: in D$_2$O, signals at 100 MHz are shown below δ ppm). 179.79(s), 177.00(s), 176.11(s), 170.93(s), 170.77(s), 166.42(d), 162.24(s), 159.63(s), 134.46(s), 118.40(s), 79.67(s), 72.70(d), 67.07(t), 66.01(d), 63.26(t), 57.58(d), 57.03(d), 56.52(d), 43.61(t), 41.18(t), 37.35(t), 32.68(t), 28.98(t), 28.65(t), 27.52(t), 23.50(t). (s: singlet, , d: doublet, t: triplet, q: quartet).

(9) Amino acid analysis: in 5.5N-HCl, 110° C., the sample was hydrolized for 15 hours. Serine and α-aminoadipic acid were detected.
(10) Thin layer chromatography (TLC): Spot film cellulose (Tokyo Chemical Industries, Ltd., Japan) Solvent system, acetonitrile: 3% ammonium sulfate (1:1), Rf=0.58.
(11) High performance liquid chromatography (HPLC); column, YMC pack A312 (Yamamura Chemical Laboratories), mobile phase, 2% methanol/0.01 M phosphate buffer (pH 3.0), 2 ml/min. Rt=3.7 (min).

The following properties are in common among the components A, B, C, D, E and F.
(12) Solubility: Easily soluble: water, aqueous acetone, aqueous alcohol. Sparingly soluble: dimethylsulfoxide, methanol, acetone, ethyl acetate.
(13) Color reaction: Positive ninhydrin, Greig-Leaback, Sakaguchi reactions. Negative: Barton reaction potassium permanganate.

TAN-592B . monohydrochloride
(1) Appearance: white powder.
(2) Molecular weight: SIMS method, $(M+H)^+$ 791.
(3) Molecular formula: $C_{29}H_{46}N_{10}O_{14}S.HCl.(2H_2O)$.

| (4) Elemental analysis (%): | |
|---|---|
| Found*[1] | Calcd.*[2] |
| C, 40.00 ± 2.0 | C, 40.35 |
| H, 5.83 ± 1.0 | H, 5.95 |
| N, 15.64 ± 1.5 | N, 16.23 |
| | O, 29.65 |
| S, 4.30 ± 1.0 | S, 3.71 |
| Cl, 4.53 ± 1.5 | Cl, 4.11 |

*[1], *[2] The same conditions as those of A.

(5) UV spectrum: $\lambda_{max}^{H2O}$ 260±2 nm ($E_{1\ cm}^{1\%}$ =108±20).
(6) CD spectrum: $[\theta]_{226\pm2}^{H2O}$ −31000±5000 and $[\theta]_{258\pm2}^{H2O}$ +29000±5000.
(7) IR spectrum: FIG. 2 3400, 3080, 2950, 1780, 1730, 1660, 1520, 1390, 1250, 1170, 1060, 980, 860, 520.
(8) $^{13}$C-NMR spectrum: 179.85(s), 177.20(s), 176.24(s), 174.41(s), 171.13(s), 166.42(d), 162.23(s), 159.61(s), 134.55(s), 117.97(s), 79.67(s), 72.86(d), 67.10(t), 66.00(d), 63.89(t), 63.19(t), 59.10(d), 57.40(d), 57.18(d), 56.30(d), 43.58(t), 41.46(t), 37.36(t), 32.74(t), 29.33(t), 28.66(t), 27.41(t), 23.52(t).
(9) Amino acid analysis: (the same conditions as that of A). Serine (about 2 moles) and α-aminoadipic acid were detected.
(10) TLC: (the same conditions as that of A) Rf=0.61.
(11) HPLC: (the same conditions as that of A) Rt=4.2 (min.).

TAN-592C . dihydrochloride
(1) Appearance: white powder.
(2) Molecular weight: SIMS method, $(M+H)^+$ 862.
(3) Molecular formula: $C_{32}H_{51}N_{11}O_{15}S.2HCl.(4-H_2O)$.

| (4) Elemental analysis (%): | |
|---|---|
| Found*[1] | Calcd.*[2] |
| C, 38.04 ± 2.0 | C, 38.17 |
| H, 6.30 ± 1.0 | H, 6.11 |
| N, 14.30 ± 1.5 | N, 15.30 |
| | O, 30.19 |
| S, 3.18 ± 1.0 | S, 3.18 |

-continued

| (4) Elemental analysis (%): | |
|---|---|
| Found*[1] | Calcd.*[2] |
| Cl, 7.76 ± 1.5 | Cl, 7.04 |

*[1] The same conditions as those of A.
*[2] The sample contains 4 moles of water.

(5) UV spectrum: $\lambda_{max}^{H2O}$ 260±2 nm($E_{1\ cm}^{1\%}$ =97±20).

(6) CD spectrum: $[\theta]_{226\pm2}^{H2O}$ −28000±5000 and $[\theta]_{258\pm2}^{H2O}$ +26000±5000.

(7) IR spectrum: FIG. 3 3420, 3070, 3000, 2950, 1780, 1735, 1660, 1520, 1450, 1390, 1250, 1165, 1060, 860, 520.

(8) $^{13}$C-NMR spectrum: 179.52(s), 178.64(s), 176.16(s), 175.71(s), 174.49(s), 173.94(s), 169.48(s), 166.45(d), 162.54(s), 159.67(s), 132.57(s), 123.59(s), 79.79(s), 72.33(d), 66.82(t), 66.47(d), 64.06(t), 63.87(t), 58.97(d), 58.28(d), 56.26(d), 56.21(d), 51.93(d), 43.62(t), 41.46(t), 37.25(t), 32.33(t), 29.33(t), 28.91(t), 27.35(t), 23.41(t), 19.47(q).

(9) Amino acid analysis: (the same conditions as that of A) Serine (about 2 moles), alanine and α-aminoadipic acid were detected.

(10) TLC: (the same conditions as that of A) Rt=0.68.

(11) HPLC: (the same conditions as that of A) Rt=4.6(min.).

TAN-592D . dihydrochloride
(1) Appearance: white powder.
(2) Molecular weight: SIMS method, (M+H)+ 661.
(3) Molecular formula: $C_{25}H_{40}N_8O_{11}S \cdot 2HCl \cdot (3H_2O)$.

| (4) Elemental analysis: | |
|---|---|
| Found*[1] | Calcd.*[1] |
| C, 37.51 ± 2.0 | C, 38.12 |
| H, 6.28 ± 1.0 | H, 6.14 |
| N, 14.10 ± 1.5 | N, 14.23 |
|  | O, 28.44 |
| S, 4.00 ± 1.0 | S, 4.07 |
| Cl, 9.94 ± 1.5 | Cl, 9.00 |

*[1] The same conditions as those of A.
*[2] The sample contains 3 moles of water.

(5) UV spectrum: $\lambda_{max}^{H2O}$ 260±2 nm ($E_{1\ cm}^{1\%}$ =110±20).

(6) CD spectrum: $[\theta]_{226\pm2}^{H2O}$ −25000±5000 and $[\theta]_{256\pm2}^{H2O}$ +22000±5000.

(7) IR spectrum: FIG. 4 3420, 3075, 2950, 1770, 1735, 1670, 1550, 1460, 1400, 1260, 1170, 1110, 1065, 870, 540.

(8) $^{13}$C-NMR spectrum: 179.36(s), 176.10(s), 175.86(s), 170.69(s), 170.18(s), 168.18(s), 159.69(s), 132.59(s), 122.91(s), 72.69(d), 67.04(t), 63.21(t), 62.08(d), 60.24(d), 57.58(d), 56.57(d), 56.39(d), 43.64(t), 41.19(t), 37.41(t), 32.36(t) 28.97(t), 28.71(t), 27.51(t), 23.71(t).

(9) Amino acid analysis: (the same conditions as those of A) Serine and α-aminoadipic acid were detected.

(10) TLC: (the same conditions as those of A) Rf=0.62.

(11) HPLC: (the same conditions as those of A) Rt=7.9 (min.).

TAN-592E . dihydrochloride
(1) Appearance: white powder.
(2) Molecular weight: SIMS method, (M+H)+ 748.
(3) Molecular formula: $C_{28}H_{45}N_9O_{13}S \cdot 2HCl \cdot (H_2O)$.

| (4) Elemental analysis: | |
|---|---|
| Found*[1] | Calcd.*[2] |
| C, 39.71 ± 2.0 | C, 40.10 |
| H, 5.87 ± 1.0 | H, 5.89 |
| N, 14.85 ± 1.5 | N, 15.03 |
|  | O, 26.71 |
| S, 3.90 ± 1.0 | S, 3.82 |
| Cl, 7.46 ± 1.5 | Cl, 8.45 |

*[1] The same conditions as those of A.
*[2] The sample contain 1 mole of water.

(5) UV spectrum: $\lambda_{max}^{H2O}$ 260±2 nm ($E_{1\ cm}^{1\%}$ 91±20).

(6) CD spectrum $[\theta]_{226\pm2}^{H2O}$ −24000±5000 and $[\theta]_{256\pm2}^{H2O}$ +17000±5000.

(7) IR spectrum: FIG. 5 3400, 3060, 2950, 1765, 1730, 1660, 1540, 1460, 1390, 1240, 1170, 1110, 1060, 1020, 870, 810, 500.

(8) $^{13}$C-NMR spectrum 179.41(s), 176.44(s), 176.20(s), 174.23(s), 171.02(s), 168.01(s), 159.66(s), 133,50(s), 121.05(s), 72.83(d), 67.11(t), 63.92(t), 63.12(t), 62.06(d), 60.21(d), 58.99(d), 57.38(d), 56.82(d), 56.27(d), 43.62(t), 41.40(t), 37.49(t), 32.54(t), 29.23(t), 28.59(t), 27.40(t), 23.78(t).

(9) Amino acid analysis: (the same conditions as those of A) Serine (about 2 moles) and α-aminoadipic acid were detected.

(10) TLC: (the same conditions as those of A) Rf=0.64. HPLC: (the same conditions as those of A) Rt=9.6(min.).

TAN-592F . dihydrochloride
(1) Appearance: white powder.
(2) Molecular weight: SIMS method, (M+H)+ 819.
(3) Molecular formula: $C_{31}H_{50}N_{10}O_{14}S \cdot 2HCl \cdot (4\text{-}H_2O)$.

| (4) Elemental analysis (%): | |
|---|---|
| Found*[1] | Calcd.*[2] |
| C, 38.00 ± 2.0 | C, 38.63 |
| H, 6.87 ± 1.0 | H, 6.27 |
| N, 14.35 ± 1.5 | N, 14.53 |
|  | O, 29.88 |
| S, 3.10 ± 1.0 | S, 3.33 |
| Cl, 7.78 ± 1.5 | Cl, 7.36 |

*[1] The same conditions as those of A.
*[2] The sample contains 4 moles of water.

(5) UV spectrum: $\lambda_{max}^{H2O}$ 260±2 nm ($E_{1\ cm}^{1\%}$ =90±20).

(6) CD spectrum: $[\theta]_{226\pm2}^{H2O}$ −32000±5000 and $[\theta]_{256\pm2}^{H2O}$ +20000±5000.

(7) IR spectrum: FIG. 6 3420, 3070, 2950, 1770, 1735, 1660, 1540, 1460, 1395, 1340, 1250, 1160, 1110, 1065, 530.

(8) Amino acid analysis: (the same conditions as those of A) Serine (about 2 moles), alanine and α-aminoadipic acid were detected.

(9) TLC: (the same conditions as those of A) Rf=0.67.

(10) HPLC: (the same conditions as those of A) Rt=10.1 (min.).

The physico-chemical properties of Antibiotic TAN-591. hydrochloride obtained in Example 2 which appears hereinafter are shown below.

TAN-591A . dihydrochloride
(1) Appearance: white powder.
(2) Molecular weight: SIMS method, (M+N)+ 676.

(3) Molecular formula: $C_{26}H_{41}N_7O_{12}S\cdot 2HCl\cdot(2H_2O)$.

| (4) Elemental analysis: | |
|---|---|
| Found*1 | Calcd.*2 |
| C, 40.38 ± 2.0 | C, 39.79 |
| H, 6.53 ± 1.0 | H, 6.04 |
| N, 12.81 ± 1.5 | N, 12.50 |
|  | O, 28.54 |
| S, 4.07 ± 1.0 | S, 4.09 |
| Cl, 8.40 ± 1.5 | Cl, 9.04 |

*1 The sample was dried over diphosphorus pentoxide for 8 hours at 60° C. under reduced pressure.
*2 The value is calculated as the sample contains 2 moles of water.

(5) Ultraviolet absorption (UV) spectrum: $\lambda_{max}^{H2O}$ 260±2 nm ($E_1{}_{cm}{}^{1\%}$ =118±20).

(6) Circular dichloism (CD) spectrum: $[\theta]_{226\pm 2}{}^{H2O}$ −34000±5000 and $[\theta]_{258\pm 2}{}^{H2O}$ +27000±5000.

(7) Infrared (IR) spectrum: Main wave number (cm$^{-1}$) in KBr tablet, FIG. 7. 3420, 3250, 3080, 2950, 1780, 1735, 1675, 1515, 1410, 1360, 1280, 1160, 1060, 980, 860, 520.

(8) Nuclear magnetic resonance ($^{13}$C-NMR) spectrum: in D$_2$O, signals at 100 MHz are shown below (δ ppm) 179.74(s), 177.19(s), 176.16(s), 170.90(s), 170.66(s), 166.42(d), 162.12(s), 134.89(s), 117.77(s), 79.70(s), 72.71(d), 67.12(t), 66.02(d), 63.22(t), 57.58(d), 57.35(d), 56.67(d), 42.22(t), 41.21(t), 37.36(t), 32.77(t), 31.28(t), 29.30(t), 28.62(t), 25.08(t), 23.50(t). (s: singlet, d: doublet, t: triplet, q: quartet)

(9) Amino acid analysis: in 5.5 N-HCl, 110° C., the sample was hydrolized for 15 hours. Serine and α-aminoadipic acid were detected.

(10) Thin layer, chromatography (TLC): spot film, cellulose (Tokyo Chemical Industries, Ltd.) Solvent system, acetonitrile: 3% ammonium sulfate (1:1), Rf=0.45.

(1) High performance liquid chromatography (HPLC): column, YMC pack A312 mobile phase, 5% methanol/0.01 M phosphate buffer (pH 3.0), 2 ml/min. Rt=2.4 (min.).

The following properties are in common among components A, B and C.

(12) Solubility: Easily soluble: water, aqueous acetone, aqueous alcohol. Sparingly soluble: dimethylsulfoxide, methanol, acetone, ethyl acetate.

(13) Color reaction: Positive: Ninhydrine, Greig-Leaback reactions. Negative: Barton reaction, potassium permanganate, Sakaguchi reaction.

TAN-591B . dihydrochloride
(1) Appearance: white powder.
(2) Molecular weight: SIMS method, (M+H)+ 763.
(3) Molecular formula: $C_{29}H_{46}N_8O_{14}S\cdot 2HCl\cdot(2H_2O)$.

| (4) Elemental analysis (%): | |
|---|---|
| Found*1 | Calcd.*2 |
| C, 39.34 ± 2.0 | C, 39.95 |
| H, 6.02 ± 1.0 | H, 6.01 |
| N, 12.52 ± 1.5 | N, 12.85 |
|  | O, 29.38 |
| S, 4.40 ± 1.0 | S, 3.68 |
| Cl, 7.57 ± 1.5 | Cl, 8.13 |

*1,*2 Same conditions as those of A.

(5) UV spectrum $\lambda_{max}^{H2O}$ 260±2 nm ($E_1{}_{cm}{}^{1\%}$ =124±20).

(6) CD spectrum: $[\theta]_{226\pm 2}{}^{H2O}$ −39000±5000 and $[\theta]_{258\pm 2}{}^{H2O}$ +29000±5000.

(7) IR spectrum: FIG. 8 3400, 3270, 3080, 2970, 1780, 1735, 1670, 1530, 1410, 1260, 1160, 1060, 980, 875, 520.

(8) $^{13}$C-NMR spectrum: 179.69(s), 177.19(s), 176.21(s), 174.14(s), 171.04(s), 170,89(s), 166.38(d), 162.07(s), 134.95(s), 117.55(s), 79.68(s), 72.84(d), 67.09(t), 66.00(d), 63.90(t), 63.10(t), 59.00(d), 57.41(d), 57.36(d), 56.37(d), 42.25(t), 41.41(t), 37.35(t), 32.77(t), 31.47(t), 29.20(t), 28.60(t), 24.94(t), 23.49(t).

(9) Amino acid analysis: (the same conditions as those of A) Serine (about 2 moles) and α-amino-adipic acid were detected.

(10) TLC: (the same conditions as those of A) Rf=0.47.

(11) HPLC: (the same conditions as those of A) Rt=2.8 (min.).

TAN-591C . trihydrochloride
(1) Appearance: white powder.
(2) Molecular weight: SIMS method, (M+H)+ 834.
(3) Molecular formula: $C_{32}H_{51}N_9O_{15}S_3\cdot HCl\cdot(4H_2O)$.

| (4) Elemental analysis (%) | |
|---|---|
| Found*1 | Calcd.*2 |
| C, 36.74 ± 2.0 | C, 37.85 |
| H, 6.31 ± 1.0 | H, 6.16 |
| N, 11.74 ± 1.5 | N, 12.42 |
|  | O, 29.94 |
| S, 3.48 ± 1.0 | S, 3.16 |
| Cl, 11.86 ± 1.5 | Cl, 10.48 |

*1 The same conditions as those of A.
*2 The sample contains 4 mole of water.

(5) UV spectrum: $\lambda_{max}^{H2O}$ 260±2 nm ($E_1{}_{cm}{}^{1\%}$ =110±20).

(6) CD spectrum: $[\theta]_{226\pm 2}{}^{H2O}$ −57000±5000 and $[\theta]_{258\pm 2}{}^{H2O}$ +39000±5000.

(7) IR spectrum: FIG. 9 3440, 3270, 3080, 2950, 1780, 1740, 1675, 1530, 1410, 1250, 1150, 1060, 960, 800, 540.

(8) Amino acid analysis: (the same conditions as those of A) Serine (about 2 moles), alanine and α-aminoadipic acid were detected.

(9) TLC: (the same conditions as those of A) Rf=0.51.

(10) HPLC: (the same conditions as those of A) Rt=3.3 (min.).

In said properties, the absolute configurations of serine, alanine and α-aminoadipic acid were determined by HPLC method as the L-form, L-form and D-form, respectively.

From said physico-chemical properties, it is assumed that the chemical structures of said compounds are those shown by the formula (I).

The biological activities of the compounds (I) are mentioned hereinafter.

The antimicrobial spectra of TAN-592 (hydrochloride) are shown in Table 1.

TABLE 1

| Test organism | Minimal inhibitory concentration (μg/ml)* TAN-592 | | | | | |
|---|---|---|---|---|---|---|
| | A | B | C | D | E | F |
| Escherichia coli NIHJ JC-2 | 12.5 | 25 | 25 | >50 | >50 | >50 |
| Pseudomonas aeruginosa IFO 3080 | 50 | >50 | >50 | >50 | >50 | >50 |
| Serratia marcescens IFO 12648 | 50 | 25 | 50 | >50 | >50 | >50 |
| Alcaligenés faecalis IFO 13111 | 3.13 | 6.25 | 6.25 | 25 | 25 | 12.5 |
| Proteus vulgalis IFO 3988 | 12.5 | 12.5 | 25 | 50 | 50 | 50 |
| Salmonella typhimurium IFO 12529 | 50 | 25 | 25 | 50 | 50 | >50 |
| Klebsiella pneumoniae IFO 3317 | 50 | 50 | 50 | >50 | >50 | >50 |
| Citrobacter freundii IFO 12681 | 50 | 25 | >50 | >50 | >50 | >50 |
| Acinetobacter calcoaceticus IFO 12552 | 1.56 | 1.56 | 3.13 | >50 | >50 | >50 |
| Staphylococcus aureus FDA 209P | >50 | >50 | >50 | >50 | >50 | 50 |
| Bacillus subtilis NIHJ PCI 219 | 12.5 | 12.5 | 12.5 | 1.56 | 1.56 | 1.56 |
| Bacillus megaterium IFO 12108 | 12.5 | 12.5 | 12.5 | 1.56 | 1.56 | 1.56 |
| Brevibacterium thiogenitalis ATCC 19240 | 3.13 | 6.25 | 6.25 | 3.13 | 3.13 | 3.13 |

(Note):
*Culture medium: 17.5 g of Bacto antibiotic medium 3 (Difco), 5 g of Bacto yeast extract (Difco), 20 g of Bacto agar (Difco), 1 l of distilled water; pH not adjusted.
The amount of inoculated microorganism: 1 loopful of about $10^6$/ml of microorganism suspension.

TAN-592A, B, C is stable to various kinds of β-lactamases. Stability to two β-lactamases employing *Escherichia coli* PG8 as a test organism is shown in Table 2.

TABLE 2

| β-lactamase | TAN-592 | | | PCG | CPC | CMC |
|---|---|---|---|---|---|---|
| | A | B | C | | | |
| not added | 28 | 29 | 29 | 22 | 33 | 34 |
| penicillinase*[1] | 28 | 29 | 29 | —*[3] | 32 | 34 |
| cephalosporinase*[2] | 28 | 29 | 29 | — | — | — |

The data shows the diameter of growth inhibition zone (mm). Culture medium: Nutrient agar medium (pH 7.0) containing diaminopimeric acid, PCG: benzylpenicillin, CPC: cephalosporin C, CMC: cephamycin C, Concentration of drug: 100 μg/ml in all the cases.

The therapeutic effect of TAN-592B.hydrochloride to infectious disease in mice is shown below.

TABLE 3

| Infection organism | Route of administration | $ED_{50}$ (mg/kg) |
|---|---|---|
| Escherichia coli 0-111* | subcutaneous | 16.2 |

*Intraperitoneal infection

When Antibiotic TAN-592B hydrochloride was administered subcutaneously in a dose of 1 g/kg to mice, no death was observed, and therefore Antibiotic TAN-592 is considered to be low in toxicity.

As is clear from said data, Antibiotic TAN-592 has an inhibitory activity to gram positive and gram negative bacteria, and is low in toxicity to mammals. TAN-592A, B and C are stable to various kinds of β-lactamases.

Furthermore, antimicrobial spectra of TAN-591 (hydrochloride) to various microorganisms are shown in Table 4.

TABLE 4

| Test organism | Minimal inhibitory concentration (μg/ml)* TAN-591 | | |
|---|---|---|---|
| | A | B | C |
| Escherichia coli NIHJ JC-2 | 25 | 25 | 50 |
| Pseudomonas aeruginosa IFO 3080 | 100 | >100 | >100 |
| Serratia marcescens IFO 12648 | 25 | 50 | 50 |
| Alcaligenes faecalis IFO 13111 | 6.25 | 12.5 | 50 |
| Proteus vulgalis IFO 3988 | 25 | 25 | 50 |
| Salmonella typhimurium IFO 12529 | 25 | 25 | 50 |
| Klebsiella pneumoniae IFO 3317 | 50 | 50 | 50 |
| Citrobacter freundii IFO 12681 | 50 | 50 | 100 |
| Acinetobacter calcoaceticus IFO 12552 | 1.56 | 3.13 | 3.13 |
| Staphylococcus aureus FDA 209P | >100 | >100 | >100 |
| Bacillus subtilis NIHJ PCI219 | 12.5 | 25 | 25 |
| Bacillus megaterium IFO 12108 | 12.5 | 12.5 | 25 |
| Brevibacterium thiogenitalis ATCC 19240 | 6.25 | 6.25 | 12.5 |

(Note):
*Medium: Bacto antibiotic medium (Difco) 17.5 g, Bacto yeast extract (Difco) 5 g, Bacto agar (Difco) 20 g, distilled water 1 l, pH not adjusted.
The amount of inoculated microorganism: 1 loopful of about $10^6$/ml of microorganism suspension.

TAN-591A, B, C are stable to various β-lactamases. The results of stability test of the antibiotic to two β-lactamases employing *Escherichia coli* PG8 as a test organism are shown in Table 5.

TABLE 5

| β-lactamase | TAN-591 | | | PCG | CPC | CMC |
|---|---|---|---|---|---|---|
| | A | B | C | | | |
| not added | 22.5 | 23 | 22 | 22 | 33 | 34 |
| penicilinase | 22 | 23 | 22 | —*[3] | 32 | 34 |
| cephalosporinase | 22 | 23 | 22 | — | — | — |

The data shows the diameter of growth inhibition zone (mm). Culture medium: Nutrient agar medium (pH 7.0) containing diaminopimeric acid, PCG: benzylpenicillin, CPC: cephalosporin C, CMC: cephamycin C. Concentration of drug: 100 μg/ml in all the cases.

The therapeutic effect of TAN-591A.hydrochloride to infectious disease in mice is shown below.

TABLE 6

| Infection organism | Route of administration | ED$_{50}$ (mg/kg) |
|---|---|---|
| Escherichia coli 0-111* | subcutaneous | 16.2 |

*Intraperitoneal infection

When Antibiotic TAN-591A hydrochloride was administered subcutaneously a dose of 1 g/kg to mice, no death was observed, and therefore Antibiotic TAN-591 is considered to be low in toxicity.

As is evident from these data, the compound (I) exhibits antimicrobial activity against gram-positive and gram-negative bacteria, and is an antibiotic with low toxicity to mammals, etc. And the compound (I) wherein $R^1$ is formylamino is stable to $\beta$-lactamase producing strain. Therefore, the compound (I) can be used in the treatment of infectious diseases caused by bacteria in mammals (e.g., mouse, rat, rabbit, dog, human being, etc.).

In order to use the compound (I) for example as a therapeutic agent against infectious disease caused by bacteria, the compound (I) is administered in a dosage form with a pharmaceutically acceptable carrier or excipient, for example as an injection by parenteral route, to the above mammals subcutaneously or intramuscularly in the dose of about 1 to 50 mg/kg/day, preferably about 5 to 20 mg/kg/day. As preparations for oral administration the compound (I) is formulated into capsules, which are administered in the dose of about 1 to 100 mg/kg/day as the compound (I), preferably about 5 to 50 mg/kg/day.

In addition, the compound (I) can be used as a bactericide. The compound (I), for example, is made into a liquid preparation having the compound (I) in concentration of about 0.01 to 0.1 w/v % dissolved in distilled water, and an ointment containing about 0.2 to 20 mg, preferably about 1 to 10 mg of the compound (I) per gram of the preparation, and they can be applied for sterilization and disinfection of hands, feet, eyes, ears, etc. of the above mammals by coating them on these parts of the body.

The compound (I) is also a highly valuable compound as an intermediate for the synthesis of new drugs.

The compound (I) of the present invention is a cephem antibiotic produced by bacteria, and according to the method of the present invention, the objective compound of this invention can be produced by the fermentation process in large amounts in a shortened period of time.

Furthermore, the compound (I) of the present invention, which is stable to cephalosporinases, is promising as a pharmaceutical for clinical uses.

The compound (I) is also a highly valuable compound as an intermediate for the synthesis of cephem compounds.

Figure 1:
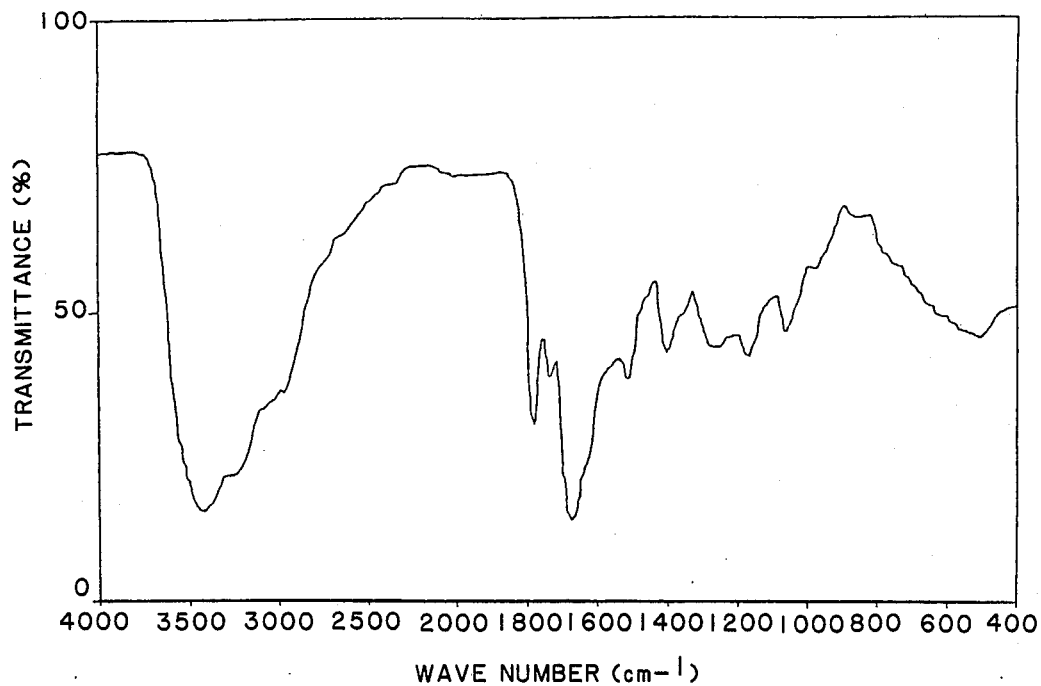
FIGS. 1, 2, 3, 4, 5, 6, 7, 8 and 9 represent infrared absorption spectra of Antibiotic TAN-592A.dihydrochloride, B.hydrochloride, C.dihydrochloride, D.dihydrochloride, E.dihydrochloride, F.dihydrochloride, Antibiotic TAN-591A dihydrochloride, B.dihydrochloride and C.trihydrochloride, respectively.
Figure 2:
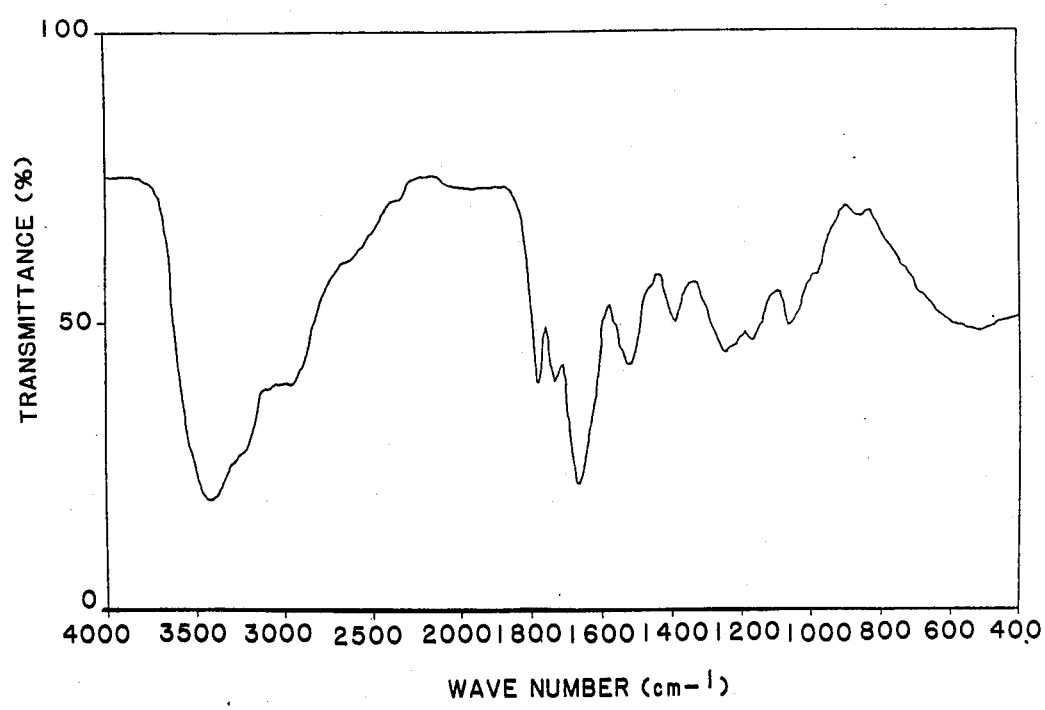
Figure 3:
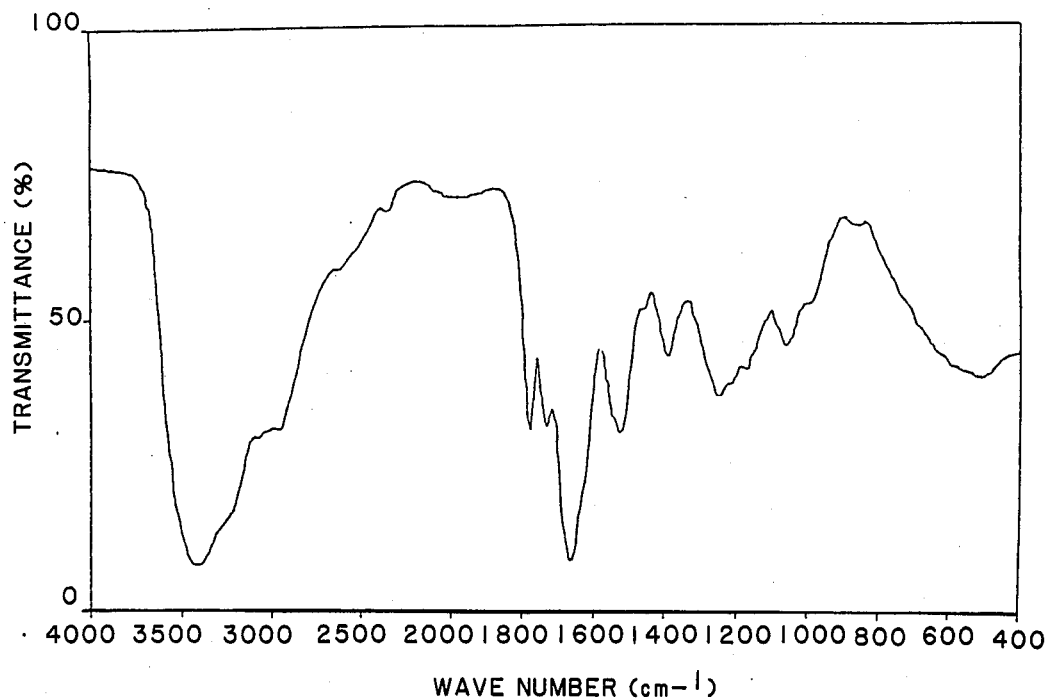
Figure 4:
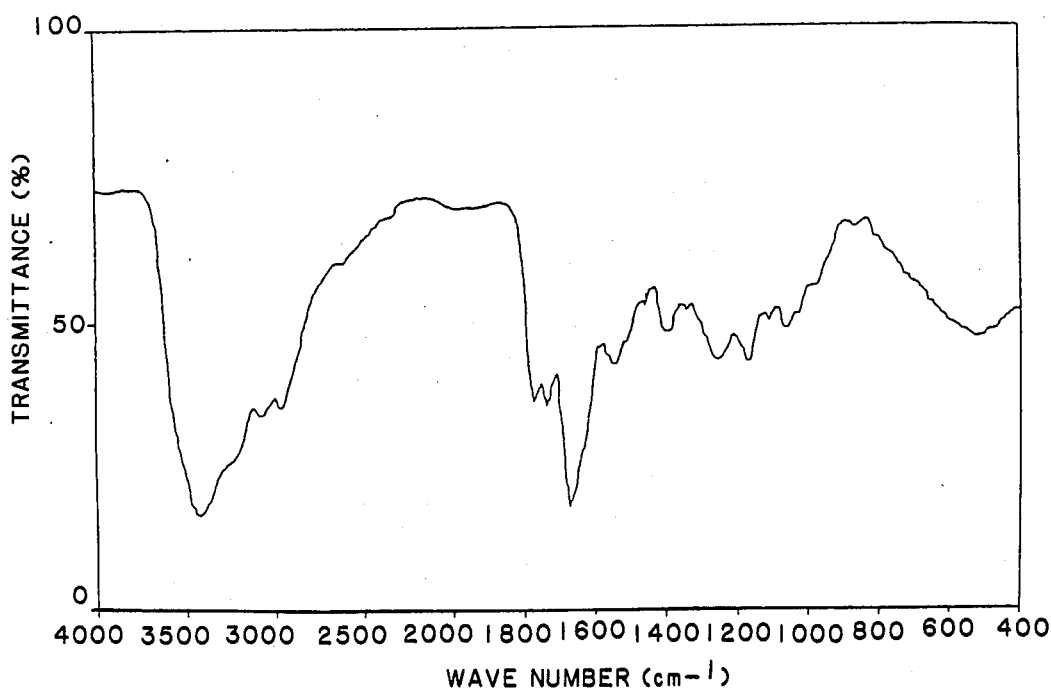
Figure 5:
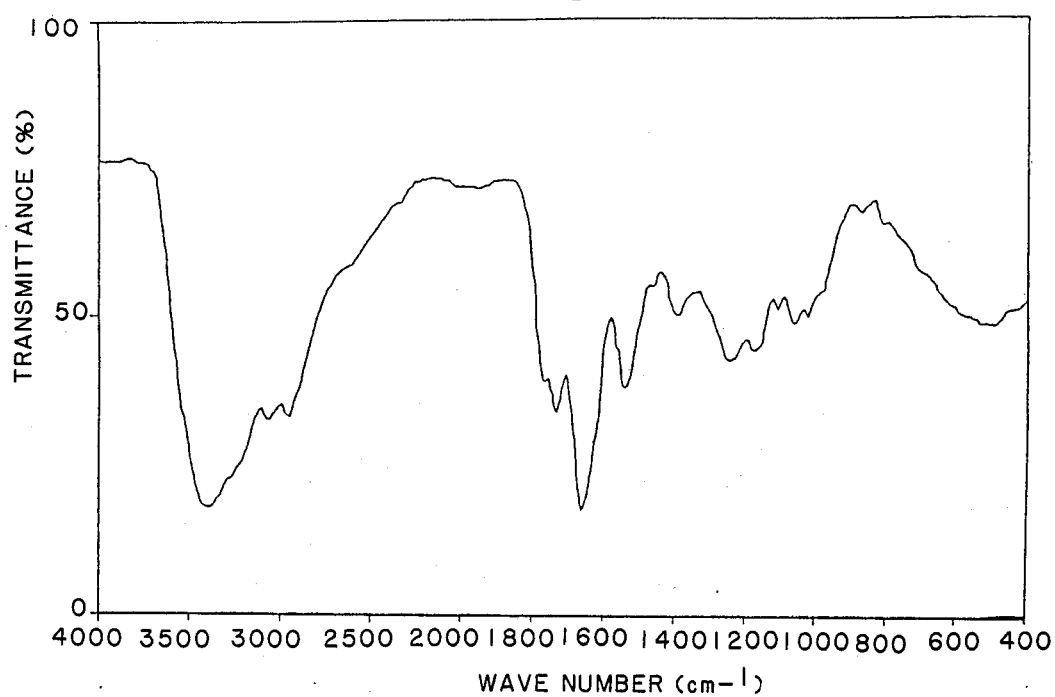
Figure 6:
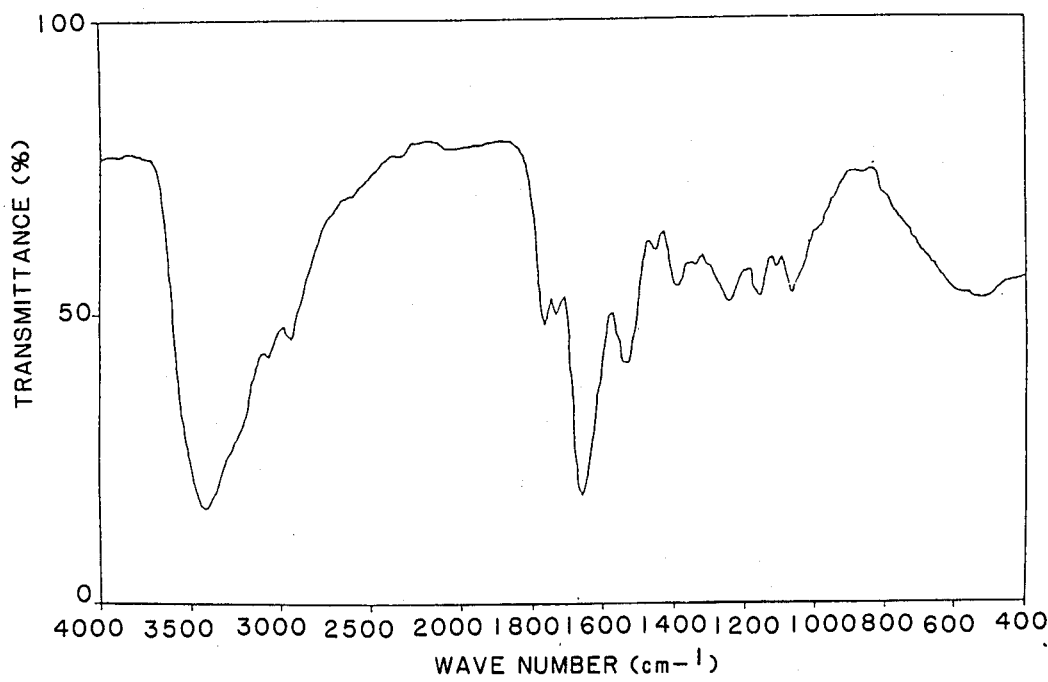
Figure 7:
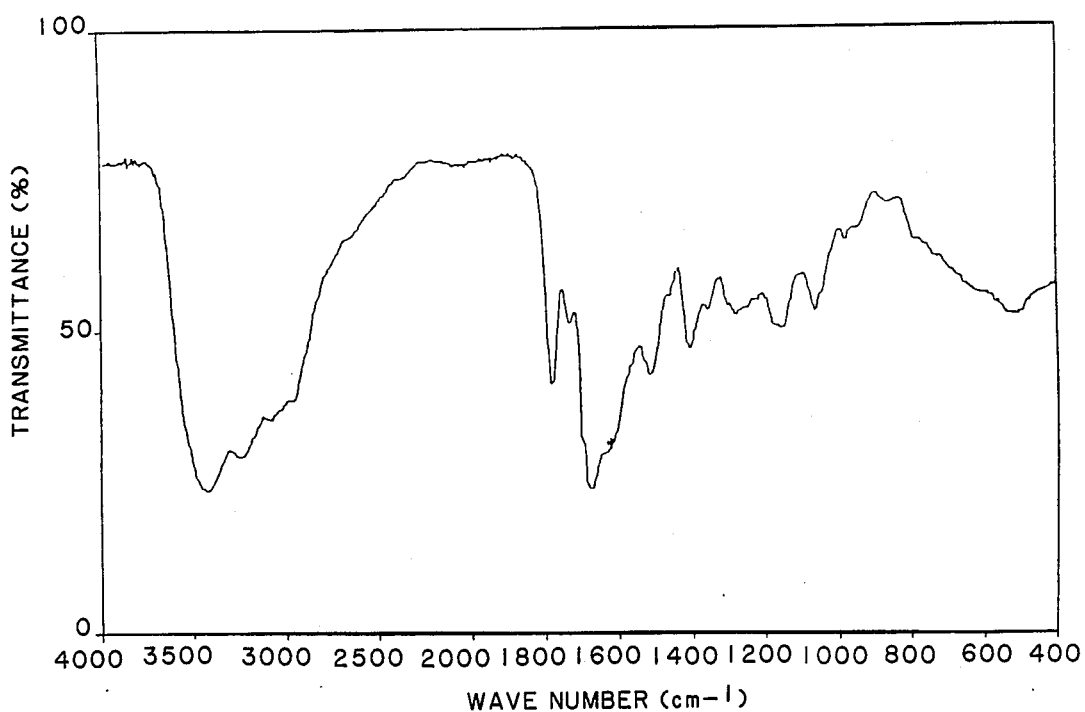
Figure 8:
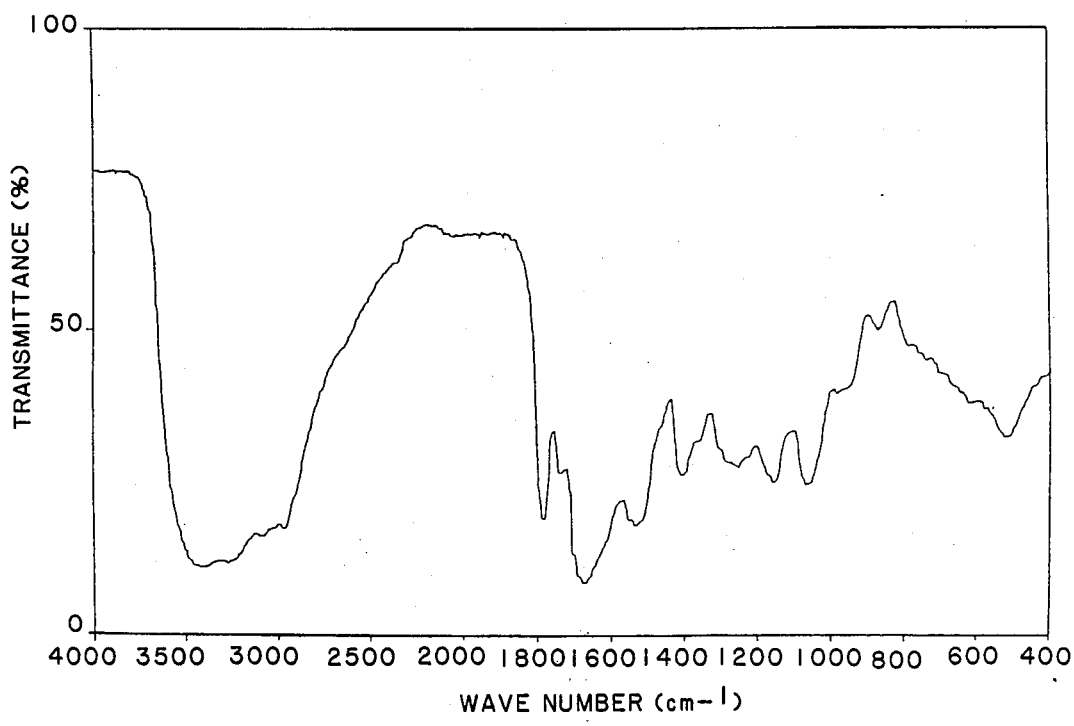
Figure 9:
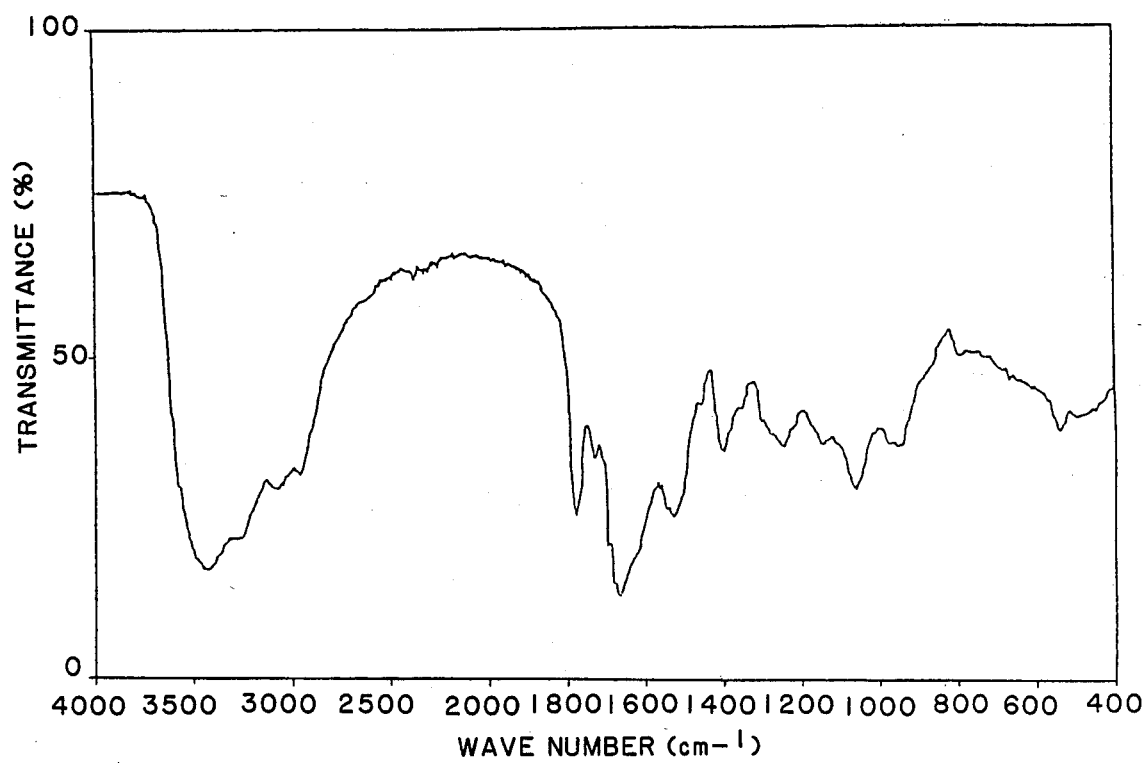

The examples are described in the following to illustrate the present invention more in detail. The term % in the culture medium means a weight/volume %, unless otherwise noted.

EXAMPLE 1

Xanthomonas lactamgena YK-280 (IFO 14330, FERM BP-635) isolated from a plant sample collected at Tsuge, Ayama District, Mie Prefecture, Japan, which was grown on a nutrient agar slant, was used to inoculate a 2-l Sakaguchi flask containing 500 ml of a culture medium comprising an aqueous solution (pH 7.0) having the composition of 2% of glucose, 3% of soluble starch, 1% of raw soybean flour, 0.3% of corn steep liquor, 0.5% of Polypepton (produced by Daigo Nutritive Chemicals, Japan) and 0.3% of sodium chloride and 0.5% of precipitating calcium carbonate admixed, and incubated on a reciprocating shaker at 24° C. for 48 hours. The total volume of the culture broth thus obtained was transferred to a tank with a 200 l capacity containing 120 l of the above-described culture medium admixed with 0.05% of an antifoam, Actcol (Takeda Chemical Industries, Ltd.,Japan), and incubated at 24° C. for 48 hours, with aeration at the rate of 120 l/min and agitation at 120 r.p.m. The total volume of the culture broth was transferred to a tank with a 2000 l capacity containing 1200 l of culture medium comprising an aqueous solution (whose pH was not adjusted) having the composition of 3% of dextrin, 3% of raw soybean flour and 0.2% of Polypepton admixed with 0.5% of precipitating calcium carbonate and 0.05% of Actcol, and incubated at 24° C. for 66 hours, with aeration at the rate of 1200 l/min. and agitation at 100 r.p.m.

The culture (1140 l) obtained by the above procedure was adjusted at pH 6.0 with 2 N hydrochloric acid, admixed with Hyflo-Super Cel(Johns Manville Products, U.S.A.), filtered and washed with water to yield a filtrate (1370 l). The filtrate was adjusted to pH 6.3, and passed through a column packed with Dowex-50W (Na$^+$ type 50 to 100 mesh, 25 l). After the column was washed with water (75 l), elution was conducted with 2 M aqueous sodium chloride solution. The eluate was passed through a column packed with activated carbon (15 l), and after the column was washed with water (45 l), elution was carried out with 8% isobutanol-N/100 hydrochloric acid (105 l). The eluate was adjusted to pH 6.2 and concentrated to 12 l, and the concentrate was adjusted to pH 7.3 and passed through a column packed with Diaion HP-20 (10 l). The column was washed with 0.01 M phosphate buffer (pH 7.3, 20 l), and elution was conducted with 0.01 M phosphate buffer (pH 2.5, 100 l).

The eluate was passed through a column of activated carbon (2.5 l) and washed with water (6 l), and elution was carried out with 8% isobutanol-N/200 hydrochloric acid (18 l). The eluate was concentrated to 1.6 l, and the concentrate was adjusted to pH 7.3 and passed through a column packed with Diaion HP-20 (50 to 100 mesh, 2 l). The column was washed with 0.01 M phosphate buffer (pH 7.3, 4 l), and elution fractionation was conducted with 0.01 M phosphate buffer (pH 3.0, 20 l). Individual fractions were subjected to analysis by liquid chromatography, and separated into two groups of fractions containing TAN-592A, B and C as a principal component and fractions containing TAN-592D, E and F as a principal component.

The fractions containing TAN-592A, B and C as a principal component as obtained in the above were collected and passed through a column of activated carbon (500 ml), and after the column was washed with water (1.5 l), elution was conducted with 8% isobutanol-N/200 hydrochloric acid (3 l). After the eluate was concentrated, the concentrate was passed through a column packed with CM-Sephadex C-25 (Na+ type, 0.8 l), and elution fractionation was carried out with 0.02M aqueous sodium chloride solution (40 l). Individual fractions were subjected to analysis by liquid chromatography, and the fractions showing a single peak of TAN-592A and B, respectively, and the fractions containing TAN-512C as a principal component were collected.

The fractions containing TAN-592A solely were collected and passed through a column of activated carbon (0.3 l), and after the column was washed with water (0.9 l), elution was carried out with 8% isobutanol-N/200 hydrochloric acid (2.1 l). The eluate was concentrated, and the concentrate was lyophilized to give a white powder (1.5 g) of TAN-592 dihydrochloride. In the same manner as described above, there were obtained a white powder (2.0 g) of TAN-592B monohydrochloride from the fractions containing TAN-592B solely and a crude powder (1.9 g) of TAN-592C from the fractions containing TAN-592C as a principal component.

The crude powder (0.7 g) of TAN-592C was passed through a column packed with CM-Sephadex C-25 (Na+ type, 100 ml), and elution fractionation was carried out with 0.02M aqueous sodium chloride solution (3 l). Individual fractions were subjected to analysis by liquid chromatography, and the fractions containing TAN-592 as a principal component were collected and passed through a column of activated carbon (30 ml). After the column was washed with water (100 ml), elution was conducted with 8% isobutanol-N/200 hydrochloric acid (210 ml), and the eluate was concentrated.

The concentrate was subjected to HPLC for separation with use of YMC-Pack SH-343 (20 mmφ × 250 mm, produced by Yamamura Chemical Laboratories, Japan), and elution was carried out with 0.01 M phosphate buffer (pH 3.0). Individual fractions were subjected to analysis by liquid chromatography, and the fractions showing a single peak were collected. The effective fractions were adjusted to pH 7.3 with 1 N NaOH, readjusted to pH 3.0 with 1 N HCl and passed through a column packed with activated carbon (20 ml). After the column was washed with water (80 ml), elution was carried out with 8% isobutanol-water (200 ml), and the eluate was concentrated and lyophilized to give a white powder (110 mg) of TAN-592C dihydrochloride.

The fractions containing TAN-592D, E and F as a principal component as obtained in the above were collected and passed through a column of activated carbon (200 ml), and after the column was washed with water (600 ml), elution was carried out with 8% isobutanol-N/200 hydrochloric acid (1.4 l). After the eluate was concentrated, the concentrate was passed through a column packed with CM-Sephadex C-25 (Na+ type, 300 ml), and elution fractionation was conducted with 0.02M aqueous sodium chloride solution (15 l). Individual fractions were subjected to analysis by liquid chromatography, and the fractions containing TAN-592D, E and F as a principal component, respectively, were collected.

The fractions containing TAN-592D as a principal component were collected, and passed through a column of activated carbon (80 ml), and after the column was washed with water (250 ml), elution was carried out with 8% isobutanol-N/200 hydrochloric acid (560 ml). The eluate was concentrated and the concentrate was lyophilized to give a crude powder (1236 mg) of TAN-592D. By conducting the same procedure with the fractions containing TAN-592E and F as a principal component, respectively, there were obtained a crude powder (1560 mg) of TAN-592E and a crude powder (656 mg) of TAN-592F.

The crude powder (1236 mg) of TAN-592D was subjected to HPLC for separation with use of YMC-Pack SH-343, and elution fractionation was carried out with 1% methanol-0.01M phosphate buffer (pH 3.0). Individual fractions were subjected to analysis by liquid chromatography, and the fractions showing a single peak were collected. The effective fractions were adjusted to pH 7.3 with 1 N NaOH, readjusted to pH 3.0 with 1 N HCl and passed through a column packed with activated carbon (50 ml), and after the column was washed with water (200 ml), elution was conducted with 8% aqueous isobutanol (400 ml). The eluate was concentrated, and the concentrate was lyophilized to yield a white powder (332 mg) of TAN-592D dihydrochloride.

In the same manner as described above, the crude powders of TAN-592E and F were subjected to HPLC for separation to give a white powder (501 mg) of TAN-592E dihydrochloride and a white powder (46 mg) of TAN-592F dihydrochloride, respectively.

EXAMPLE 2

A culture of *Xanthomonas lactamgena* YK-278 (IFO 14351, FERM BP-636) grown on a nutrient agar slant was used to inoculate 15 Erlenmeyer flasks of a 200-ml capacity each containing 40 ml of a culture medium comprising of an aqueous solution (pH 7.0) having the composition of 2% of glucose, 3% of soluble starch, 1% of raw soybean flour, 0.3% of corn steep liquor, 0.5% of Polypepton and 0.3% of sodium chloride admixed with 0.5% of precipitating calcium carbonate, and incubated on a rotary shaker at 24° C. for 24 hours to make the resulting culture broth a seed culture.

16 l of a culture medium containing 3.0% of dextrin, 1.5% of corn gluten meal, 0.2% of Polypepton, 0.1% of sodium thiosulfate and 0.5% of precipitating calcium carbonate (pH 7.0) was distributed in 40 ml portions into Erlenmeyer flasks of a 200-ml capacity and sterilized at 120° C. for 20 minutes. 1 ml of the seed culture was used to inoculate the individual Erlenmeyer flasks each containing the sterilized culture medium, and incubated on a rotary shaker at 17° C. for 90 hours with the agitation at a rate of 230 r.p.m.

The culture broth (16 l) as obtained in the above manner was adjusted to pH 6.5 with 2 N hydrochloric acid, admixed with water (16 l) and centrifuged to give a filtrate (32 l).

The filtrate was passed through a column packed with Dowex-50W (Na+ type, 50 to 100 mesh, 0.5 l), and after the column was washed with water (1.5 l), elution was carried out with 2M aqueous sodium chloride solution (10 l). The eluate was passed through a column of activated carbon (0.3 l), and after the column was washed with water (1 l), elution was carried out 8% isobutanol-N/200 hydrochloric acid (2.2 l). The eluate was adjusted to pH 6.2 and concentrated to 0.5 l, and the concentrate was adjusted to pH 7.3 and passed through a column packed with Diaion HP-20 (0.6 l). The column was washed with 0.01M phosphate buffer (pH 7.3, 1.6 l), and elution was carried out with 0.01M phosphate buffer (pH 3.0, 6 l).

The three portions of eluates were respectively passed through a column of activated carbon (80 ml), and after the column was washed with water (300 ml), elution was carried out with 8% isobutanol-N/200 hydrochloric acid (600 ml). The eluate was lyophilized to give crude substances I (402 mg), II (760 mg) and III (448 mg).

It was confirmed by HPLC that in the crude substance II, there was included TAN-592A, B and C, in the crude substance III, there was included TAN-592D, E and F.

The crude substances were purified by the manner of Example 1 to give 18 mg of TAN-592 (hydrochloride), 39 mg of B, 35 mg of C, 12 mg of D, 15 mg of E and 24 mg of F.

The crude substance I (400 mg) was dissolved in water (100 ml), and the solution was passed through a column packed with CM-Sephadex C-25 (Na+ type, 50 ml), followed by elution fractionation with 0.02M aqueous sodium chloride solution (1.5 l). Individual fractions were subjected to analysis by liquid chromatography, and fractions containing TAN-591A, B and C as a principal component, respectively, were collected.

The fractions containing TAN-591A, B and C as a principal component, respectively, were passed through columns of activated carbon (10 ml for each column), and after the columns were washed with water (30 ml for each column), elution was effected with 8% aqueous isobutanol solutions (70 ml for each elution). The eluates were concentrated, and each concentrate was subjected to HPLC for separation using YMC-Pack SH-343 (20 mm$\phi \times$250 mm), followed by elution fractionation with 0.01M phosphate buffer (pH 4.5). Individual fractions were subjected to analysis by liquid chromatography, and fractions showing a single peak were collected. The effective fractions were adjusted to pH 7.3 with 1 N NaOH, readjusted to pH 3.0 with 1 N HCl and passed through a column packed with activated carbon (5 ml). After the column was washed with water (20 ml), elution was carried out with 8% aqueous isobutanol solution (50 ml), and the eluate was concentrated and lyophilized to give white powders of TAN-591A (3 mg), B (18 mg) and C (22 mg) hydrochlorides.

EXAMPLE 3

A culture broth (100 l), which was obtained by cultivating *Xanthomonas lactamgena* YK-280 (IFO 14330, FERM BP-635), was subjected to centrifugation to give wet cells. The wet cells were poured into 10 l of 70% aqueous acetone and the mixture was stirred for 30 minutes. The resultant was filtered, and the filtrate was concentrated. The concentrate was subjected to column chromatography of activated carbon (100 ml), and the column was eluted with 50% aqueous acetone (500 ml). The concentrate of the eluates was subjected to column chromatography of Amberlite IRA-68 (acetate form, 50 ml), and the column was eluted with 0.2M sodium acetate solution (350 ml).

The active portions of the eluates was subjected to column chromatography of activated carbon, desalting procedure, concentration, and freeze-drying. Thus obtained crude powder was subjected to preparative reverse phase high performance chromatography, to give deacetylcephalosporin C (1.4 mg). The Rf value of TLC, Rt value of HPLC, UV, CD, IR and 1H-NMR spectra and bioautography were identical with those of authentic sample.

EXAMPLE 4

The culture broth (100 l) of *Xanthomonas lactamgena* YK-278 (IFO 14351, FERM BP-636), which was cultured in the same manner as that of Example 2, was subjected to the same purification procedure as Example 3 to give 2 mg of deacetylcephalosporin C.

What we claim is:

1. A compound of the formula:

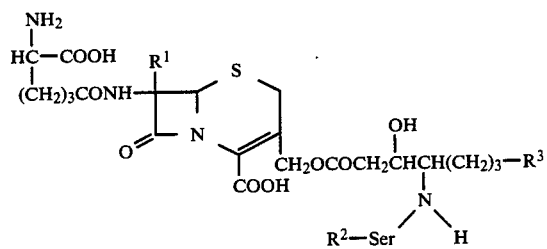

wherein $R^1$ is hydrogen or formylamino, $R^2$ is a member selected from the group consisting of hydrogen, Ser— and Ala—Ser—, and $R^3$ is —NH—C(=NH)—NH$_2$ or —CH$_2$NH$_2$, or a salt of said compound.

2. A compound as claimed in claim 1, wherein $R^1$ is formylamino.

3. A compound as claimed in claim 1, wherein $R^1$ is hydrogen.

4. A compound as claimed in claim 1, wherein $R^2$ is hydrogen.

5. A compound as claimed in claim 1, wherein $R^2$ is Ser—.

6. A compound as claimed in claim 1, wherein $R^2$ is Ala—Ser—.

7. A compound as claimed in claim 1, wherein $R^3$ is —NH—C(=NH)—NH$_2$.

8. A compound as claimed in claim 1, wherein $R^3$ is —CH$_2$NH$_2$.

9. A compound as claimed in claim 1, wherein $R^1$ is formylamino, $R^2$ is hydrogen and $R^3$ is —NH—C(=NH)—NH$_2$.

10. A compound as claimed in claim 1, wherein $R^1$ is formylamino, $R^2$ is Ser— and $R^3$ is —NH—C(=NH)—NH$_2$.

11. A compound as claimed in claim 1, wherein $R^1$ is formylamino, $R^2$ is Ala—Ser— and $R^3$ is —NH—C(=NH)—NH$_2$.

12. A compound as claimed in claim 1, wherein $R^1$ is formylamino, $R^2$ is hydrogen and $R^3$ is —CH$_2$NH$_2$.

13. A compound as claimed in claim 1, wherein $R^1$ is formylamino, $R^2$ is Ser— and $R^3$ is —CH$_2$NH$_2$.

14. A compound as claimed in claim 1, wherein $R^1$ is formylamino, $R^2$ is Ala—Ser— and $R^3$ is —CH$_2$NH$_2$.

* * * * *